US005698221A

United States Patent [19]
Patel et al.

[11] Patent Number: 5,698,221
[45] Date of Patent: Dec. 16, 1997

[54] WATER-DISPERSIBLE TABLETS

[76] Inventors: Suryakant Dahyabhai Patel; Michael John Desmond Gamlen, both of The Wellcome Foundation Limited, Temple Hill, Dartford, Kent, Da1 5AH; Krystyna Elzbieta Fielden, Broomer Cottage, Churchgate, Chashunt, Hertfordshire, EN8 9NB, all of United Kingdom

[21] Appl. No.: 374,728

[22] PCT Filed: Jul. 27, 1993

[86] PCT No.: PCT/GB93/01586

§ 371 Date: May 9, 1995

§ 102(e) Date: May 9, 1995

[87] PCT Pub. No.: WO94/02147

PCT Pub. Date: Feb. 3, 1994

[30] Foreign Application Priority Data

Jul. 27, 1992 [GB] United Kingdom ............... 9215908

[51] Int. Cl.⁶ .......................................... A61K 9/20
[52] U.S. Cl. .................. 424/464; 424/458; 424/489; 424/470
[58] Field of Search .......................... 424/464, 470, 424/458, 489, 180; 523/400

[56] References Cited

U.S. PATENT DOCUMENTS

| | | |
|---|---|---|
| 3,427,379 | 2/1969 | Barry et al. . |
| 3,432,593 | 3/1969 | Shepard . |
| 3,567,829 | 3/1971 | Leonia et al. . |
| 4,072,535 | 2/1978 | Short et al. . |
| 4,086,335 | 4/1978 | Bruscato et al. . |
| 4,159,345 | 6/1979 | Takao et al. . |
| 4,209,513 | 6/1980 | Torode et al. . |
| 4,251,512 | 2/1981 | Moore et al. . |
| 4,251,518 | 2/1981 | Moore et al. ............... 424/180 |
| 4,304,773 | 12/1981 | Wong et al. . |
| 4,305,502 | 12/1981 | Gregory et al. . |
| 4,322,449 | 3/1982 | Voss et al. . |
| 4,369,308 | 1/1983 | Trubiano . |
| 4,371,516 | 2/1983 | Gregory et al. . |
| 4,414,192 | 11/1983 | Michaelson . |
| 4,517,179 | 5/1985 | Raghunathan . |
| 4,600,579 | 7/1986 | Salpekar et al. . |
| 4,602,017 | 7/1986 | Sawyer et al. . |
| 4,631,305 | 12/1986 | Guyer et al. . |
| 4,661,521 | 4/1987 | Salpekar et al. . |
| 4,711,777 | 12/1987 | Tan et al. . |
| 4,757,090 | 7/1988 | Salpekar et al. . |
| 4,774,083 | 9/1988 | Tan et al. . |
| 4,781,925 | 11/1988 | Michelucci et al. . |
| 4,832,956 | 5/1989 | Gergely et al. . |
| 4,837,031 | 6/1989 | Denton . |
| 4,847,249 | 7/1989 | Sawyer . |
| 4,904,477 | 2/1990 | Ho et al. . |
| 4,910,023 | 3/1990 | Botzolakis et al. . |
| 4,925,676 | 5/1990 | Sellassie et al. . |
| 4,927,639 | 5/1990 | Sellassie et al. . |
| 4,950,484 | 8/1990 | Olthoff et al. . |
| 4,965,072 | 10/1990 | Alexander et al. . |
| 4,968,517 | 11/1990 | Gergely et al. . |
| 4,970,078 | 11/1990 | Holinej . |
| 4,999,200 | 3/1991 | Casillan . |
| 5,006,345 | 4/1991 | Lang . |
| 5,037,658 | 8/1991 | Urban et al. . |
| 5,047,247 | 9/1991 | Milovac et al. . |
| 5,049,586 | 9/1991 | Ortega et al. . |
| 5,064,656 | 11/1991 | Gergely et al. . |
| 5,069,910 | 12/1991 | Kovacic et al. . |
| 5,073,377 | 12/1991 | Alexander et al. . |
| 5,085,869 | 2/1992 | Olthoff et al. . |
| 5,087,454 | 2/1992 | Duerholz et al. . |

FOREIGN PATENT DOCUMENTS

| | | |
|---|---|---|
| 53042/90 | 12/1990 | Australia . |
| AU 89096/91 | 6/1992 | Australia . |
| 0 261 595 81 | 3/1988 | European Pat. Off. . |
| 0 294 933 | 5/1988 | European Pat. Off. . |
| 0 305 843 A2 | 3/1989 | European Pat. Off. . |
| 0372934 | 6/1989 | European Pat. Off. . |
| 0 350 701 A2 | 1/1990 | European Pat. Off. . |
| 0 372 934 A2 | 6/1990 | European Pat. Off. . |
| 0 391 851 A1 | 10/1990 | European Pat. Off. . |
| 0 459 819 A2 | 12/1991 | European Pat. Off. . |
| 0 265 226 | 5/1992 | European Pat. Off. . |
| 2016622 | 10/1971 | Germany . |
| 43-24078 | 10/1968 | Japan . |
| 207678 | 11/1986 | New Zealand . |
| 222701 | 6/1990 | New Zealand . |
| 777516 | 6/1957 | United Kingdom . |
| 837451 | 6/1960 | United Kingdom . |
| 1 317 400 | 5/1973 | United Kingdom . |
| 1 443 023 | 7/1974 | United Kingdom . |
| 1 421 964 | 1/1976 | United Kingdom . |
| 1 480 175 | 7/1977 | United Kingdom . |
| 1 480 188 | 7/1977 | United Kingdom . |
| 2 249 957 | 5/1992 | United Kingdom . |
| 83/00809 | 3/1983 | WIPO . |
| 87/05804 | 10/1987 | WIPO . |
| 91/03241 | 3/1991 | WIPO . |
| 91/07174 | 5/1991 | WIPO . |

OTHER PUBLICATIONS

Japan abstract kokai No. 1-93541; vol. 13; 2 pages.
Hager's Handbook of Pharmaceutical Practice, 4th Edition, vol. 7; part B pp. 271–281.
Paracja Polska (1966); No. 7; pp. 505–509.
Acta Poloniae Pharmaceutica; 15; No. 4, 1968; four pages.
Britain Pharmacopia 1988, vol. II, pp. 891–895.
R. P. Shangraw; University of Maryland; "Specialty Tablets and Capsules" pp. 427–440–1990.

(List continued on next page.)

*Primary Examiner*—Thurman K. Page
*Assistant Examiner*—William E. Benston, Jr.
*Attorney, Agent, or Firm*—Nixon & Vanderhye

[57] ABSTRACT

A water-dispersible tablet comprising 2-amino-2-(4-methylpiperazin-1-yl)-5-(2,3,5-trichlorophenyl)pyrimidine together with a swellable clay disintegrating agent and a further disintegrating agent. The tablet can be used in the treatment of neurodegenerative and other neurological disorders of the central nervous system, the etiology of which includes excessive release of neurotransmitter glutamate, including Alzheimer's disease, cerebral ischemic damage, chronic pain and epilepsy.

13 Claims, No Drawings

OTHER PUBLICATIONS

International Search Report CT/GB 93/01586.
Rudnic et al, Drug Development and industrial Pharmacy; 7(3), pp. 347–358; (1981).
Patel N.K., Kennon L. and Levinson S.R., Pharmaceutical Suspensions, Chapter 16 from the Theory and Practice of Industrial Pharmacy (ed Lachman, Lieberman and Xanig).
Lowenthal, J. Pharm Sci, vol. 61; No. 11, Nov. 1972, pp. 1695–1711.
Holstius et al.; J. Amer. Pharm. Sci (1952), 41,505.
Patel et al., Indian J. Pharm., 26,313 (1964).
Patel, et al., Indian J. Pharm., 28,244 (1966).
Smeczi, et al. Acta Pharm. Hungary., 40,124 (1970) through Int. Pharm Abst, 8, 1283 (1971).
Billups et al., Amer J. Pharm. 136.25 (1964).
Patel, et al., Indian J. Pharm., 25,220 (1963).
Shotton et al. J. Pharm. Sci., 65 (1976) 1170–1174.
British Specifications: 2119355, 2157170, 590725, 501960, Canadian No. 2013918.
Abstracts of Japanese Patent Application (Kokai laid open); 54 129129, 56–127309, 57–11911, 57,11913, 57–56434, 58–194816, 60–209518, 62–227729, 63–30313, 64–42347, 2–111620, 2–145501, 3–264502, 2–59515.
Search report (same as EPO search) in corresponding Belgium and French national applications.
Court proceedings: Plaintuff's Statement of Case.
Court proceedings: Defence and Counterclaim.
Court proceedings: Further and Bener Particulars of Plaintiff's Statement of Case.
Court proceedings Agree Draft Minutes of Order.
Court proceedings: Reply and Defense to Counterclaim.
Pennwalt Corp.; Raghunathan, Y. Mar. 28, 1984: pp 1–33; 27678; Cellulose and Starch.
Zyms SA: 222701, (22) Nov. 26, 1987; pp 1–2; A Water–Dispersable Tablet Comprising An active Medicament Contained Within Microparticles At Least One Disintegrant And A Swellable Material.
Salo et al, Pharmazhl, 20,5 (1965)—through Int. Pharm Abst 3, 1342d (1966).
Birmancevic et al, Arh. Farm. (1981), 31 (1–2), 45–54.
Birmancevic et al., Acta, Pharmaceutica Jugoslavia (1974), 24, pp 237–240.
Birmancevic et al. Arch. Farm (1970), 28, 21–28.
Borzonuv et al., through ChemAbstr., 69 1097q (1968).
Borzonuv et al., through Chem Abst., 71 3385y (1969).
Selmeczi, et al. through Chem Abst. 70 14395q (1969).
Saufrulin, et al., through Chem Abst. 58, 13727a (1963).
Kuever et al., J. American Pharm. Ass. Sci, 17,365 (1928).
Shotton et al. J. Pharm Pharmac., 1972 24, 798–803.
Veegum—The Natural Ingredient: R.T. Vanderbilt & Co., p. 9.
Veegum—The Supernatural Ingredient: R.T. Vanderbilt & Co., Booklet (1987).
Veegum—The Versatile Ingredient for Pharmaceutical Formulations: R.T. Vanderbilt & Co., Booklet.
Pharmasorb: Lawrence Industries. pp. 1–10 (1986).
Polargel White Bentonite: American Colloid Co., Booklet.
Mastery in Refinement—Magnabrite & Polargel: American Colloid Co.
Wai, et al., "Applications of the Montmorillonites in Tablet Making," J. Pharm. Sci., 55: 1244–1248 (1966).
Wai & Banker, "Some Physicochemical Properties of the Montmorillonites," J. Pharm. Sci., 55: 1215–1220 (1966).

Granberg, et al., "The Use of Dried Bentonite as a Disintegrating Agent in Compressed Tablets of Thyroid," J. Am. Pharm. Assoc. Sci., 43: 648–651 (1949).
Gross, et al., "A Comparative Study of Tablet DIsintegrating Agents," J. Am. Pharm. Assoc. Sci., 41: 157–161 (1952).
Firouzabadian, et al., "Some Recently Developed Chemicals as Disintegrating Agents for Compressed Tablets," J. Am. Pharm. Assoc. Sci., 43: 248–250 (1954).
Ward, et al., "Evaluation of Tablet Disintegrants," Drug Cosmetic Ind. 91: 35–36, 92, 110–111 (1962).
Nair, et al., "Studies on Disintegration of Compressed Tablets I. Effect on Disintegration of the Procedure Used in Incorporating the Disintegrating Agent," J. Am. Pharm. Assoc. Sci., 46: 131–134 (1957).
Patel, et al., "Veegum as Binding Agent for Compressed Tablets," Indian J. Pharm., 19: 4–10 (1957).
Feinstein, et al., "Comparative Study of Selected Disintegrating Agents," J. Pharm. Sci. 55: 332–334 (1966).
Varley, A., "The Generic Inequivalence of Drugs," JAMA, 206: 1745–1748 (1968).
Delonca, et al., "Study of the Activity of Some Disintegrants as a Function of Procedure and of the Solubility of the Active Principles," J. Pharm. Belg. 26(4): 447–458 (1971)—English Translation.
Wagner, et al., "In Vivo and In Vitro Availability of Commercial Warfarin Tablets," J. Pharm. Sci. 60: 666–677 (1971).
McGinty, et al., "Optimization of Slow–Release Tablet Formulations Containing Montmorillonite I. Properties of Tablets," Drug Development and Industrial Pharmacy 6: 399–410 (1980).
Bargava, et al., "An Evaluation of Smecta as a Tablet Disintagrant and Dissolution Aid," Drug Development and Industrial Pharmacy 17: 2093–2102 (1991).
Barr, M., "In Pharmaceutical Systems . . . Clays as Dispersion Stabilizers," J. Amer. Pharm. Assoc. Sci. Ed. 46: 486–493 (1957).
US Pharmacopoeia, pp. 579, 1573, 1574, 1534 and 1535 (1985).
British Pharmacopoeia, pp. 27, 18, 51, 52, 62, 323–325 (1985).
Martindale, The Extra Pharmacopoeia, 29th Edition, pp. 4, 1077, 1092 and 1433.
The Handbook of Pharmaceutical Excipients, pp. 9–11, 150–152, 166–169.
Armstrong, N., "Tableting" from Pharmaceutics: The Science of Dosage Form Design, (Ed. Aulton): 647–668 (1988).
Rubinstein, M., "Tablets" from Pharmaceutics: The Science of Dosage Form Design, (Ed. Aulton): 304–321 (1988).
Rudnic, et al., "Oral Solid Dosage Forms," from Remington's Pharmaceutical Sciences (ed. Gennaro), pp. 1633–1665 (1990).
Disanto, A., "Bioavailability and Bioquivalency Testing," from Remington's Pharmaceutical Sciences (ed. Gennaro), pp. 1451–1458 (1990).
Banker, et al., "Tablets," from The Theory and Practice of Industrial Pharmacy, pp. 293–345.
Marshall, et al., "Tablet Dosage Forms," from Modern Pharmaceutics (eds., Banker, G. & Rhodes, C.) pp. 355–425 (1990).
Shangraw, R., "Specialty Tablet and Capsules," from Modern Pharmaceutics (eds. Banker, G. & Rhodes, C.) pp. 427–440 (1990).

WATER-DISPERSIBLE TABLETS

The present invention relates to a water-dispersible tablet formulation containing 4-amino-2-(4-methylpiperazin-1-yl)-5-(2,3,5-trichlorophenyl)pyrimidine.

European Patent Specification No. 372934 discloses the compound 4-amino-2-(4-methylpiperazin-1-yl)-5-(2,3,5-trichlorophenyl)-pyrimidine (hereinafter referred to as "AMTP") and their use in the treatment of neurodegenerative and other neurological disorders of the central nervous system, the aetiology of which includes excessive release of neurotransmitter glutamate, including Alzheimer's disease, cerebral ischemic damage, chronic pain and epilepsy.

In order to be able to administer AMTP to patients to achieve the optimum therapeutic benefit from the drug, it would be desirable to present the drug in a pharmaceutical formulation that is capable of rapid dispersion in water.

Following extensive research and investigation, we have now discovered a tablet formulation for AMTP that is capable of rapid dispersion in water.

According to one aspect of the present invention there is provided a water-dispersible tablet comprising within the granules of the tablet AMTP together with a pharmaceutically acceptable swellable clay disintegrating agent to provide a tablet which is capable of dispersing in water within a period of 3 minutes to provide a dispersion which is capable of passing through a sieve screen with a mesh aperture of 710 μm in accordance with the test for dispersible tablets defined in the British Pharmacopoeia, 1988, Volume II, page 895 which disclosure is herein incorporated by reference.

According to a further aspect of the present invention there is provided a water-dispersible tablet comprising within the granules of the tablet AMTP together with a pharmaceutically acceptable swellable clay disintegrating agent and a further pharmaceutically acceptable disintegrating agent to provide a tablet which is capable of dispersing in water within a period of 3 minutes to provide a dispersion which is capable of passing through a sieve screen with a mesh aperture of 710 μm in accordance with the test for dispersible tablets defined in the British Pharmacopoeia, 1988, Volume II page 895 which disclosure is herein incorporated by reference.

The above-mentioned test for dispersion time is carried out using the following apparatus and method:

Apparatus (a) A rigid basket-rack assembly supporting six cylindrical glass tubes 75.0 to 80.0 mm long, 21.5 mm in internal diameter and with a wall thickness of about 2 mm.

(b) A cylindrical disc for each tube, each 20.55 to 20.85 mm in diameter and 9.35 to 9.65 mm thick, made of transparent plastic with a relative density of 1.18 to 1.20, pierced with five holes, each 2 mm in diameter, one in the centre and the other four spaced equally on a circle of radius 6 mm from the centre of the disc. Four equally spaced grooves are cut in the lateral surface of the disc in such a way that at the upper surface of the disc they are 9.5 mm wide and 2.55 mm deep and at the lower surface 1.6 mm square.

(c) The tubes are held vertically by two superimposed transparent plastic plates 90 mm in diameter and 6 mm thick, perforated by six holes having the same diameter as the tubes. The holes are equidistant from the centre of the plate and are equally spaced from one another. Attached to the underside of the lower plate is a piece of woven gauze made from stainless steel wire 0.635 mm in diameter and having nominal mesh apertures of 2.00 mm.

(d) The plates are held rigidly in position and 77.5 mm apart by vertical metal rods at the periphery and a metal rod is also fixed to the centre of the upper plate to enable the assembly to be attached to a mechanical device capable of raising and lowering it smoothly through a distance of 50 to 60 mm at a constant frequency of between 28 and 32 cycles per minute.

(e) The assembly is suspended in the liquid medium in a suitable vessel, preferably a 1000-ml beaker. The volume of liquid is such that when the assembly is in the highest position the wire mesh is at least 15 mm below the surface of the liquid and when the assembly is in the lowest position the wire mesh is at least 25 mm above the bottom of the beaker and the upper open ends of the tubes remain above the surface of the liquid.

(f) A suitable device maintains the temperature of the liquid at 19° C. to 21° C.

The design of the basket-rack assembly may be varied provided that the specifications for the glass tubes and wire mesh are maintained.

Method

Introduce one tablet into each tube, optionally adding a disc to each tube. Suspend the assembly in the beaker containing the specified liquid and operate the apparatus for a maximum period of three minutes. Remove the assembly from the liquid. The tablets pass the test if all six have dispersed within a period of three minutes.

The test for dispersion quality (i.e. uniformity of dispersion) is carried out as follows:

Place two tablets in 100 ml of water and stir until completely dispersed. A smooth dispersion is produced which passes through a sieve screen with a nominal mesh aperture of 710 μm.

A tablet according to the invention, as well as being quickly dispersible in water, has the added advantage that it meets the British Pharmacopoeia (B. P.) test for dispersible tablets in respect of dispersion times and dispersion quality (i.e. passage through a 710 μm sieve).

Preferably the dispersion time of a tablet according to the invention is less than 2 minutes, more preferably less than 1.50 minutes and most preferably less than 1 minute.

A further advantage of the tablets according to invention is that because a relatively fine dispersion is formed the tablet may have a lower dissolution time and thus the drug may be absorbed into the blood stream much faster. Furthermore the fast dispersion times and relatively fine dispersions obtained with tablets according to the invention are also advantageous for swallowable tablets. Thus tablets according to the invention can be presented both for dispersion in water and also for directly swallowing. Those tablets according to the invention that are intended for swelling are preferably film-coated to aid swallowing. Such film-coating however increases the dispersion time up to 5 minutes determined in accordance with the above-mentioned B. P. test.

According to a further feature of the present invention therefore we provide a water-dispersible film-coated tablet comprising within the granules of the tablet AMTP together with a pharmaceutically acceptable swellable clay to provide a film-coated tablet which is capable of dispersing in water within a period of 5 minutes to provide a dispersion which is capable of passing through a sieve screen with a mesh aperture of 710 μm in accordance with the above-defined British Pharmacopoeia test for dispersible tablets subject to the variation of the said period specified in the test from 3 minutes to 5 minutes.

According to yet a further feature of the present invention therefore we provide a water-dispersible film-coated tablet comprising within the granules of the tablet AMTP together with a pharmaceutically acceptable swellable clay and a further pharmaceutically acceptable disintegrating agent to provide a film-coated tablet which is capable of dispersing in water within a period of 5 minutes to provide a dispersion which is capable of passing through a sieve screen with a mesh aperture of 710 μm in accordance with the above-defined British Pharmacopoeia test for dispersible tablets subject to the variation of the said period specified in the test from 3 minutes to 5 minutes. The references herein to tablets according to the invention include both film-coated and non-film-coated tablets.

After the dispersion has passed through the 710 μm mesh screen, there should be substantially no residue, except fragments of undissolved tablet coating or shell, remaining on the screen or adhering to the lower surface of the disc, if a disc optionally has been used; and if any residue remains, it should consist of a soft mass having no palpably firm, unmoistened core.

The particle size distribution of dispersions obtained by dispersing tablets according to the invention is set out in the following table with the increasingly preferred values being quoted from left to right.

| Particle Size (μm)* | BP Standard | Preferably | More Preferably | Most Preferably |
|---|---|---|---|---|
| <710 | <100% | 100% | 100% | 100% |
| <300 | — | >50% | >70% | >80% |
| <200 | — | — | >50% | >70% |
| <150 | — | — | — | >50% |

*(equivalent spherical volume diameter)

The term "swellable clay" as used herein includes layered clays (such as smectites), porous fibrous clay minerals, and synthetic clay materials related in structure to layered clays and porous fibrous clays.

The term "layered clays" as used herein includes substantially homogeneous layered clays and mixtures thereof, and interstratified or mixed layered clays. Substantially homogeneous layered clays includes the smectite group for example dioctahedral and trioctahedral types. Examples of dioctahedral smectites are the montmorillonite group (montmorillonoids); magnesium and other (e.g. calcium) aluminium silicates such as Veegum in its various grades e.g. Veegum, Veegum HV, Veegum F, and Veegum WG); almasilate; fullers earth (e.g. Surrey finest); American fullers earth; bentonite; beidellite; cheto montmorillonite, Wyoming montmorillonite, Utah montmorillonite; Tatalia and Chambers montmorillonites; and iron rich smectites such as nontrite (e.g. Garfield nontronite) and ferrian smectites.

Examples of trioctahedral smectites (also known as saponites) are Swinefordite, hectorite, stevensite. Examples of smectites containing more unusual elements are Volkhonsite, Medmontite, Sauconite, nickel smectites and vanadium smectites. As well as the montmorillonite group, related smectites such as vermiculites may also have application.

The term "interstratified or mixed layer clays", as used herein includes clays involving different layers arranged in a regular or irregular structure. The most common examples of such clays have generally two components in substantially equal proportions and have been given mineral names such as rectorite (mica-smectite), hydrobiotite (biotite-vermiculite), corrensiten (chlorite-smectite) allettite (talc-saponite). More irregular arrangements include illite-smectite, chlorite-smectite, and kaolinite-smectite. Further examples of interstratified clays are tosudite, tarasovite, allevardite, Japanese bentonite ("acid clays"), AWAZU acid clay, and kaolinite-smectite. Other mixed layer clays may include one or more of the following minerals: clinchlore, chamosite, nimite, thuringite, sudoite, and cookeite. Mixed layer smectities are also known e.g. interdispersed montmorillonite and beidellite layers. The layers of mixed layer clays may be homogeneous or non-homogeneous.

The term "porous fibrous clays" includes palygorskite and sepiolite such as, for example attapulgite and American fuller's earth.

The term "synthetic clay materials" as used herein includes materials related in structure to layered clays and porous fibrous clays such as synthetic hectorite (lithium magnesium sodium silicate) for example laponite$^R$.

It will be appreciated that within the scope of the invention the following classes of clays have application alone or in combination and in mixed layer clays: kaolinites, serpentines, pyrophyllites, talc, micas and brittle micas, chlorites, smectites and vermiculites, palygorskites and sepiolites. Other phyllosilicates (clay minerals) which may be employed in the tablets according to the invention are allophane and imogolite.

The following references describe the characterisation of clays of the above types: Chemistry of Clay and Clay Minerals. Edited by A. C. D. Newman. Mineralogical Society Monograph No. 6, 1987, Chapter 1; S. W. Bailey; Summary of recommendations of AIPEA Nomenclature Committee, Clay Minerals 15, 85–93; and A Handbook of Determinative Methods in Mineralogy, 1987, Chapter 1 by P. L. Hall.

Suitably the swellable clay is a pharmaceutically acceptable crystalline mineral clay having a lattice structure which expands upon hydration, preferably a pharmaceutically acceptable smectite or attapulgite clay, especially a montmorillonoid, more preferably yet a montmorillonoid chosen from the group consisting of montmorillonite, sauconite, vermiculite, bentonite and hectorite, still more preferably an aluminium magnesium silicate (also termed magnesium aluminium silicates) and most preferably Veegum$^R$. Veegum$^R$ is a complex colloidal magnesium aluminium silicate described and characterised in Technical Booklet No. 97, R. T. Vanderbilt Company, Inc., Industrial Minerals and Chemicals, 30 Winfield Street, Norwalk, Conn. 06855, U.S.A.: an especially preferred such material is Veegum F (loc. cit.).

The term "smectite" as used herein in relation to tablets of the present invention includes the smectites as exemplified herein and with reference to O'Brian P. and Williamson C. J., in "Clays and Clay Minerals vol. 38 No. 3 pp322–326, 1990" and the other clay nomenclature references set out hereinbefore.

The term "magnesium aluminium silicate" as used herein in relation to tablets of the present invention should be understood to include the Aluminium Magnesium Silicate defined in the *British Pharmacopoeia*, volume 1, pages 27–28, 1988 and the Magnesium Aluminium Silicate defined in the *United States Pharmacopoeia, National Formulary XVI*, pages 1943–1944, 1990. Advantageously, said silicate is in the form of a microfine powder having a No. 325 U.S. Standard mesh particle size, a viscosity of 250 cps (±25%) for a 5.5% (w/v) aqueous dispersion and an acid demand (the volume in ml. of 0.1N hydrochloric acid required to reduce the pH of one gram to 4) of 6–8: such a material is available as VEEGUM F (R. T. Vanderbilt Co., New York, N.Y., U.S.A.; K & K-Greeff Chemicals Ltd., Croydon, Surrey CR9 3QL, England).

The overall weight of a tablet according to the invention is variable, such as from approximately 50 to 2500 mg, more preferably 50 to 2000 mg, more preferably still 50 to 1500 mg, more preferably still 50 to 1200 mg. The amount of swellable clay can vary over a large % w/w.

Thus for a dispersible tablet according to the present invention, the intra-granular amount of swellable clay such as a crystalline mineral clay for example, magnesium aluminium silicate is suitably present in the following general ranges 0.25 to 60% w/w, preferably 0.25 to 50% w/w, more preferably 0.5 to 50% w/w, more preferably still 1 to 50% w/w, more preferably still 1 to 40% w/w, more preferably still 2 to 20% w/w, more preferably still 2.5 to 20% w/w, still more preferably 3 to 10% w/w, and most preferably 5 to 10%, most desirably about 5% w/w.

The tablets according to the invention will generally contain a pre-determined amount of AMTP depending on the desired dosage and the total weight of the tablet.

In general tablets according to the invention should contain from 5 to 95% w/w of AMTP, preferably 20 to 95% w/w, more preferably 50–95%, still more preferably 65–95%, still more preferably 65 to 85% w/w, and most preferably 70 to 85% w/w of AMTP.

Preliminary research shows that tablets of the invention will contain from 50 to 800 mg of AMTP, such as unit tablet dosages containing an equivalent (unfactorized) amount of about 50 mg, about 100 mg, about 200 mg, about 400 mg or about 800 mg of AMTP.

Based on our research, it has been found that when AMTP is present in an amount of at least 60% w/w in tablets according to the invention, we have suprisingly found that the dispersion time remains substantially constant over a range of tablet hardnesses. This is a considerable quality control advantage since in industrial manufacture it is essential to maintain a constant tablet hardness. Tablets according to the invention can thus be produced with sufficient hardness and friability so that they can easily be film-coated. A tablet according to the invention should desirably have a friability of about 2% or less, preferably 0.5% or less.

According to a further embodiment of the present invention AMTP is present in an amount of 15 to 50%, preferably 15% to 25% w/w or 35% to 45% w/w, for example in tablets containing respectively 25 mg and 60 mg of AMTP.

Based on experiments that we have carried out, it has been found that in addition to the amount of swellable clay present within the granules of the tablet, a further amount of swellable clay may be present outside the granules. At very low intra-granular amounts (such as 1% w/w or below) of a swellable clay, higher extra-granular amounts (such as about 10% w/w or more) of such clay may decrease the dispersion time, but in general extra-granular addition has little or no effect on the dispersion time. The maximum percentage(s) of the clay present within the granules and, optionally outside the granules, may be limited by other practical considerations such as poor flow and compression properties.

In addition to the swellable clay disintegrating agent, the tablets according to some aspects of the invention contain a further disintegrating agent. Examples of such disintegrating agents which may be employed in the tablets include the following agents: microcrystalline cellulose (e.g. Avicel R) 0 to 30% w/w, preferably 5 to 10% w/w, Sodium carboxymethyl cellulose (e.g. Nymcel R) 0 to 5% w/w, preferably 1 to 2% w/w, calcium carboxymethyl cellulose 0 to 20% w/w, preferably 1 to 5% w/w, modified cellulose gum (e.g. Ac-Di-Sol R) 0 to 10% w/w, preferably 1 to 5% w/w, cross-linked povidone 0 to 10% w/w, preferably 2 to 6% w/w, alginic acid and alginates 0 to 10% w/w, 2 to 5% w/w, pregelatinised starch 0 to 10% w/w, preferably 0.5 to 5% w/w, sodium starch glycollate (e.g. Explotab R, Primojel R) 0 to 10% w/w, preferably 0.5 to 5% w/w, modified corn starch (e.g. starch 1500 R) 0 to 20% w/w, preferably 1 to 10% w/w, starch (e.g. potato/maize starch ) 0 to 15% w/w, preferably 0.2 to 10% w/w, ion exchange resin such as polacrin potassium (e.g. Amberlite IRP-88) up to 5% w/w, preferably 0.5 to 2.0% w/w.

Experiments also indicate that if low-substituted hydroxypropyl cellulose (LHPC) is used a suitable dispersion can be obtained without the need for a separate wetting agent/surfactant.

According to a further embodiment of the invention, particularly preferred further disintegrating agents for use in the tablets according to the invention include sodium starch glycollate (commercially available as Explotab), LHPC, low substituted hydroxypropylmethyl cellulose (LHPMC) or a mixture of two or three thereof.

According to a further embodiment of the invention, the further disintegrating agent is employed in an mount of 1 to 5% w/w.

In addition to the disintegrating agents referred to above, it will be appreciated that the tablet according to the invention may contain other excipients conventionally used in tablet manufacture including the following:

Binders and Adhesives: we have found with some AMTP tablet formulations that if there is sufficient mount of swellable clay such as Veegum F present within the granules, then a separate binder is not required (i.e. the clay also acts as a binder). Preferably however a separate binder is present in a sufficient mount to provide a tablet having a satisfactory tablet hardness and satisfactory dispersion characterstics. The amount of binder will vary depending on the overall tablet formulation and type of binder used but general functional limits for most tablets of the invention are 0 to 25% w/w. The following binders and mounts are suitable for inclusion in a tablet according to the invention. The concentration of the binder in the granulation fluid (% w/v) is given (% w/w in tablet will vary according to the volume of granulating solution used to form a satisfactory tablet): Examples of binders are: acacia mucilage 0 to 25% w/v, preferably 1 to 5% w/v, alginic acid 0 to 20.0% w/v, preferably 1 to 5% w/v, polyvinylpyrrolidone (povidone) 0 to 15.0% w/v, preferably 0.5 to 5% w/v, gelatin 0 to 20.0% w/v, preferably 1 to 5.0% w/v, sucrose 0 to 70.0% w/v, preferably 2.0 to 20.0% w/v, starch mucilage 0 to 10.0% w/v, preferably 0.5 to 5.0% w/v, pregelatinised starch 0 to 10.0% w/v, preferably 0.5 to 5.0% w/v, starch paste 0 to 10.0% w/v, preferably 5.0 to 10.0% w/v, sodium alginate 0 to 5.0% w/v, preferably 1.0 to 3.0% w/v, sorbitol 0 to 10.0% w/v, preferably 3.0 to 10.0% w/v, tragacanth 0 to 20% w/v, preferably 5.0 to 10.0% w/v, glucose 0 to 50%, preferably 5 to 25% w/v, hydroxypropylmethyl cellulose (HPMC) 0 to 10% w/v, preferably 1.0 to 5.0% w/v, magnesium aluminium silicate 0 to 40% w/v, preferably 2 to 10% w/v, starch paste 0 to 25% w/v, preferably 5 to 15% w/v, polyvinylpyrrolidone 0 to 15% w/v, preferably 3 to 10% w/v, carboxymethylcellulose sodium 0 to 10% w/v, preferably 1 to 6% w/v, dextrin 0 to 50% w/v, preferably 5 to 25% w/v, ethyl cellulose 0 to 10% w/v, preferably 1 to 6% w/v, polyethylene glycol 0 to 5% w/v, guar gum 0 to 10% w/v, preferably 1 to 5% w/v, zein 0 to 30% w/v, preferably 1 to 10% w/v, hydroxyethyl cellulose 0 to 5% w/v, preferably 2 to 4% w/v, hydroxypropyl cellulose up to 5% w/v, preferably 2 to 4% w/v, methyl cellulose up to 20% w/v, preferably 1 to 10% w/v, polymethacrylates up to 25% w/v, preferably 5 to 10% w/v, carboxymethylcellulose calcium 0 to 20% w/v, preferably 5 to 10% w/v.

b) Fillers: These serve the purpose of bulking up the tablet to a suitable size and aiding compressibility especially in lower dosage tablets. The amount of filler depends on its type, size of tablet and amount of active compound. When the concentration of active compound is below 60% w/w, more preferably 45% w/w and most preferably below 30% w/w, an inorganic water-insoluble filler is advantageously used. Examples of water-soluble fillers (which can be used in general quantifies of 0 to 95% w/w) are: soluble lactose, compressible sugar, confectioners sugar, dextrose, mannitol, sodium chloride, sorbitol, xylitol, sodium chloride F. Examples of water-insoluble fillers (which can be used in general quantities of 0 to 93% w/w) are: calcium carbonate, magnesium carbonate, calcium phosphate (e.g. di and tri basic calcium phosphate), calcium sulphate, kaolin, microcrystalline cellulose, powdered cellulose, pregelatinized starch 5 to 75%, starch, barium sulphate, magnesium trisilicate, aluminium hydroxide.

Inclusion of a filler having a negative heat of solution in water, for example mannitol, sorbitol and xylitol, provides tablets which, in addition to being water-dispersible, are especially suitable for chewing in the mouth, the dissolving of such an excipient in the saliva producing a cool, pleasant sensation.

According to a further embodiment of the invention, particularly preferred fillers for use in the tablets according to the invention include lactose and more preferably calcium carbonate. Such fillers are generally employed in an amount of 20 to 80% for example 25 to 60% w/w, preferably 30 to 50 % w/w.

c) Lubricants: Examples of lubricants with percentage weights which are suitable for a tablet are: stearates (e.g. magnesium or calcium stearate) 0.2 to 5% w/w, preferably 0.25 to 1% w/w, talc 0.19 to 5% w/w, preferably 1 to 2% w/w, polyethylene glycol 0.19 to 5% w/w, preferably 2 to 5% w/w, liquid paraffin 0.18 to 5% w/w, preferably 2 to 5% w/w, sodium lauryl sulphate 0.19 to 5% w/w, preferably 0.5 to 2% w/w, magnesium lauryl sulphate 0.12 to 5% w/w, preferably 1 to 2% w/w, colloidal silicon dioxide 0.1 to 5% w/w, preferably 0.1 to 1.0% w/w, palmitostearate 0.01 to 5% w/w, preferably 1 to 3% w/w, stearic acid 0.01 to 5% w/w, preferably 1 to 3% w/w, zinc stearate 0.01 to 2% w/w, 0.5 to 1.5% w/w, hydrogenated vegetable oil 0.5 to 5% w/w, preferably 1 to 3% w/w. More suitably the lower value is 0.25%.

d) Wetting agents/surfactants: examples with suitable mounts are: sodium dodecyl sulphate 0 to 10% w/w, preferably 0.5 to 2% w/w, sodium lauryl sulphate 0 to 10% w/w, preferably 0.1 to 3.0% w/w, polyoxyethylene sorbitan fatty acid esters (Tweens) 0 to 3% w/w, preferably 0.05 to 1.0% w/w, polyoxyethylene stearates 0 to 2% w/w, preferably 0.05 to 1.0% w/w, sorbitan fatty acid esters (Spans) 0 to 3% w/w, preferably 0.05 to 1.0% w/w.

e) Glidants: for example, talc 0 to 5% w/w, preferably 1 to 2% w/w, starch 0 to 15% w/w, preferably 2 to 10% w/w, magnesium stearate up to 5%, preferably 0–2.0% w/w, silica derivatives generally 0 to 1% w/w, preferably 0.2 to 0.5% w/w, such as colloidal silica (e.g. Aerosil) 0 to 0–5% w/w, preferably 0.25 to 3% w/w, pyrogenic silica 0 to 2% w/w, preferably 0.25 to 1% w/w, hydrated sodium silicoaluminate 0 to 2% w/w, preferably 0.5 to 1% w/w, colloidal silicon dioxide 0 to 0.5% w/w.

f) Flavouring agents: are used in for example approximate quantifies of 0 to 5% w/w, preferably 0.25 to 2% w/w, orange, cherry and strawberry, raspberry, grape and passion fruit.

g) Sweetening agents: for example sodium saccharin 0 to 10% w/w, preferably, 0.5 to 5.0% w/w, aspartame 0 to 10% w/w, preferably 0.25 to 5.0% w/w, confectioners sugar 0 to 30% w/w, preferably 5 to 20% w/w, sorbitol 25 to 90% w/w, preferably 0.5 to 10% w/w, sucrose 0 to 85% w/w, preferably 0.5 to 20% w/w, xylitol 0–20% w/w, preferably 0.5 to 10% w/w.

Such materials may be incorporated at the appropriate stage(s) of the manufacturing process together with any other agents (e.g. colourants).

A further aspect of present invention provides a process for the preparation of a water-dispersible tablet comprising AMTP, together with a pharmaceutically acceptable swellable clay disintegrating agent which comprises bringing AMTP into association with the said swellable clay in the formation of tablet granules to provide a water-dispersible tablet which is capable of dispersing in water within a period of 3 minutes to provide a dispersion which is capable of passing through a sieve screen with a mesh aperture of 710 µm in accordance with the test for dispersible tablets defined in the British Pharmacopoeia, 1988, Volume 11, page 895.

The present invention further provides a process for the preparation of a water-dispersible tablet comprising AMTP, together with a pharmaceutically acceptable swellable clay disintegrating agent and a further disintegrating agent which comprises bringing AMTP into association with the said swellable clay and further disintegrating agent in the formation of the tablet granules to provide a water-dispersible tablet which is capable of dispersing in water within a period of 3 minutes to provide a dispersion which is capable of passing through a sieve screen with a mesh aperture of 710 µm in accordance with the test for dispersible tablets defined in the British Pharmacopoeia, 1988, Volume 11, page 895. Preferably said process comprises the steps of:

a) admixing in dry, finely-divided form AMTP with an effective mount of a pharmaceutically acceptable swellable clay and a further disintegrating agent, optionally with the addition of one or more other pharmaceutical carriers or excipients;

b) addition of a quantity of a pharmaceutically acceptable liquid sufficient to moisten the dry mixture;

c) granulation of the resulting moist mixture to form granules;

d) drying the granules and optionally blending the granules with other optional carriers or excipients such as lubricants, glidants, flavouring agents and disintegrating agents; and e) compression of the granules to form a tablet which is capable of dispersing in water within a period of 3 minutes to provide a dispersion which is capable of passing through a sieve screen with a mesh aperture of 710 µm in accordance with the above defined British Pharmacopoeia test for dispersible tablets.

Other aspects of the tablet preparation will now be discussed.

Suitably the dry mixing is effected with a mixing time of 5 minutes to 25 minutes preferably about 10 minutes.

The swellable clay can be dry mixed with AMTP and other excipients and then granulating solution added, or the clay and other excipients can be dispersed firstly in the granulating solution and then added to the AMTP and any other excipients prior to granulation.

The liquid employed to moisten the dry mixture, prior to the granulation step, is preferably aqueous, for example water or a mixture of water and a suitable alcohol such as ethanol or isopropanol.

Wet mixing or granulating times which are suitable (depending on the type of mixer used) are 5 to 20 minutes.

Suitable granule drying times and conditions (which will vary according to the type of equipment used and batch size of granules) are about 50° to 80° C., (using a dryer such as with a tray or fluid bed dryer) to obtain a moisture content generally below about 4%.

The tablets may optionally be film-coated, for example with hydroxypropylmethyl cellulose, polyethylene glycol or titanium dioxide, and/or may be scored and/or may be polished, for example with polyethylene glycol 8000. If the tablets are film-coated, this makes them easier to swallow or chew (i.e. the tablets are suitable for either dispersion in water or for direct swallowing or chewing), but the dispersion time is increased.

Tablets according to the invention containing AMTP advantageously include a magnesium aluminium silicate such as Veegum F as the swellable clay optionally together with further pharmaceutical carriers or excipients referred to above such as disintegrating agents, binders, fillers, lubricants etc.

According to one embodiment of the invention, a formulation of an AMTP dispersible tablet containing from 50 mg–800 mg AMTP comprises:

| AMTP | 65% w/w to 95% w/w, preferably 70–85% w/w |
|---|---|
| Povidone | 0.25% w/w to 5% w/w, preferably 0.5–2% w/w |
| Magnesium aluminium silicate Veegum F or bentonite | 0.5% w/w to 30% w/w, preferably 0.5–10% w/w |
| Microcrystalliine cellulose Avicel PH101 or LHPC-LH11 | 5% w/w to 25% w/w, preferably 5–15% w/w |
| Sodium starch glycollate | 0% w/w to 8% w/w, preferably 1–25% w/w |
| Magnesium stearate and if optionally film coated: | 0.25% w/w to 2% w/w, preferably 0.25–1.0% w/w |
| Opadry | 0.1% w/w to 2% w/w, preferably 0.25–1.0% w/w |
| Polyethylene glycol 8000 | 0.1% w/w to 0.5% w/w, preferably 0.1–0.2% w/w |

According to a further embodiment of the invention, a formulation of an AMTP dispersible tablet comprises AMTP, preferably in an mount of 30 to 50% w/w, preferably 35 to 45% w/w and further including one or more ingredients and proportions thereof each selected independently from the following:

| AMTP | 15% w/w to 50% w/w, preferably 45–45% |
|---|---|
| Calcium Carbonate | 25% w/w to 60% w/w, preferably 30–50% w/w |
| LHPC or LHPMC or Microcrystalline cellulose (e.g. Avicel PH101) | 5% w/w to 30% w/w, preferably 5–15% w/w |
| Veegum F or bentonite or attapulgite | 0.25% w/w to 30% w/w, preferably 2–8% w/w |
| Povidone (e.g. PVP k30) | 0.25% w/w to 5% w/w, preferably 0.5–2% w/w |
| Sodium starch glycollate | 1% w/w to 8% w/w, preferably 1–5% w/w glycollate |
| Magnesium stearate and if optionally film coated: | 0.25% w/w to 2% w/w, preferably 0.25–1.0% w/w |
| Opadry | 0.1% w/w to 2% w/w, preferably 0.25–1.0% w/w |
| Polyethylene glycol 8000 | 0.1% w/w to 0.5% w/w, preferably 0.1–0.2% w/w |

The water-dispersible tablets of AMTP according to the invention may be used to treat or prevent neurodegenerative and other neurological disorders of the central nervous system the aetiology of which includes excessive release of neurotransmatter glutamate, including Alzheimer's disease, cerebral ischaemic damage, chronic pain and epilepsy, AMTP in the above tablets may be administered in the dosages generally disclosed in European Patent Specification No. 372934, more preferably 1 to 10 mg/kg/day. Such dosages may be provided for example by the administration of a 25 mg or 50 mg tablet.

The following Examples illustrate the present invention.

| Example Number | 1 mg/tablet | 2 mg/tablet | 3 mg/tablet | 4 mg/tablet | 5 mg/tablet |
|---|---|---|---|---|---|
| AMTP* | 50.0 | 100.0 | 200.0 | 400.0 | 800.0 |
| LHPC-LH11 | 6.0 | 12.0 | 24.0 | 48.0 | 96.0 |
| Veegum F | 3.2 | 6.4 | 12.8 | 25.6 | 51.2 |
| PVP K30 | 0.7 | 1.4 | 2.8 | 5.6 | 11.2 |
| Explotab | 2.0 | 4.0 | 8.0 | 16.0 | 32.0 |
| Mg Stearate | 0.6 | 1.2 | 2.4 | 4.8 | 9.6 |
| tab weight | 62.5 mg | 125.0 mg | 250.0 mg | 500.0 mg | 1000.0 mg |
| tab diam (mm) | 5.6 | 7.4 | 8.6 | 11.0 | 14.0 |
| tab hardness | 2.0 | 4.0 | 6.0 | 10.0 | 14.0 |

| Example Number | 6 mg/tablet | 7 mg/tablet |
|---|---|---|
| AMTP* | 100.0 | 200.0 |
| LHPC-LH11 | 14.0 | 28.0 |
| Veegum F | 7.0 | 14.0 |
| Calcium Carbonate | 12.0 | 24.0 |
| PVP K30 | 2.0 | 4.0 |
| Explotab | 4.0 | 8.0 |
| Mg Stearate | 1.0 | 2.0 |
| tab weight (mg) | 140.0 mg | 280.0 mg |
| tab hardness | 6.0 kg | 8.0 kg |
| tab diam | 7.4 mm | 8.6 mm |

*unfactorized value

Method of Preparation

The tablets described in Examples 1–7 above were prepared according to the following general method:

(a) A dry mixture was made of all components except Povidone/PVP K30, sodium docusate (if present) and magnesium stearate;

(b) The Povidone/PVP K30 and sodium docusate (if present) were dissolved in 50% aqueous alcohol to form a granulation solution;

(c) The granulation solution was added to the dry mixture to form granules;

(d) The wet granules were dried in a fluid bed dryer;

(e) The granules were then sifted through a 1000 μm diameter mesh sieve; and (f) The dried granules were blended with the magnesium stearate and compressed to form tablets.

Flavouring agents where present were added at blending step (f) above.

This general method is illustrated with respect to the following specific examples.

EXAMPLES 1 TO 7

Uncoated Tablets (a) A dry mixture was made of all components except Povidone/PVP K30 and magnesium stearate using a Diosna P100 (high shear mixer—granulator) for 3 minutes.

(b) The Povidone/PVP K30 was dissolved in 50% aqueous alcohol to form a granulation solution.

(c) The granulation solution was added to an approximate quantity of 300 ml per kg dry weight to the dry mixture to form granules. Wet mixing was carried out for approximately 5 minutes.

(d) The wet granules were dried in an Aeromatic T3 fluid bed drier at a temperature of 70° C. for approximately 30 minutes. The moisture content of the granules was approximately 4%.

(e) The granules were then sifted through a 1000 μm diameter mesh sieve using a Jackson Crockatt No.7 sifter.

(f) The dried granules were blended with the magnesium stearate using a collette mixer for approximately 10 minutes and compressed to form tablets using a Manesty D3 Rotary tablet press fitted with caplet shaped punches of approximately 19.3 mm length and 9.0 mm breadth. Tablets were compressed to a weight of 1052 mg±2%.

This granule can be used to make other strengths of AMTP dispersible tablets. If gum coated tablets were required, they could be made as follows:

Steps (a) to (f) described hereabove would be repeated to form an uncoated tablet which was then film-coated by the following procedure.

The film-coating apparatus used was a Manesty Accellacota 10. The coating suspension was sprayed onto the tablet cores to a target weight increase of between 0.5–1.0% using suitable parameters of:

pan rotation speed (8.5 rpm)

spray (application rate (~20 g per min)

inlet temperature (~75° C.)

exhaust temperature (~53° C.).

A polish coat of PEG8000 was then applied to the film-coated tablets, to a further weight gain of 0.1–0.2%.

The tablets prepared in accordance with the above Examples were then tested as follows.

Tablet Evaluation Methods

1. Average tablet weight. Twenty tablets were weighed on an analytical balance and the average tablet weight calculated.

2. Tablet breaking strength (kilo pond-kp). 5 tablets were individually tested using a Schleuniger crashing strength tester, and the average breaking strength calculated.

3. Friability (% loss). 10 tablets, accurately weighed, were subjected to 10 minutes friability testing using a Roche Friabilator. The tablets were dedusted, reweighed, and the weight loss due to the friability was calculated as a percentage of the initial weight.

4. Dispersion Disintegration time DT (BP 1988). 6 tablets were tested in accordance to the above-defined BP test (without discs) for dispersible tablets. This utilises water at a temperature of 19°–21° C.

5. Dispersion Quality. In accordance with the BP uniformity of dispersion test for dispersible tablets (BP 1988 Volume II page 895), two tablets were placed in 100 ml of water at 19°–21° C. and allowed to disperse. A smooth dispersion was produced which passed through a 710 μm mesh sieve.

Granule Evaluation Methods

1. Loss on Drying (LOD). The residual moisture content of the granule (LOD) is determined on a 3–4 g sample using a Computrac moisture analyser set to 90° C. operated in accordance with the manufacturer's procedure.

2. Weight Median Diameter (WMD). A 10 g sample of granule is sifted for 2 minutes at suitable pulse and sift amplitudes in an Allen Bradley sonic sifter in accordance with manufacturer's instructions. Sieves of 710 μm, 500 μm, 355 μm, 250 μm, 150 μm, 106 μm and 53 μm were used. The WMD is calculated from the cumulative percentage undersize size distribution using a computer programme.

A particle size analysis is carried out on the dispersion of a tablet of the invention in accordance with the following method.

The particle size distribution can be determined using a Malvern 2600 particle analyser as follows. The instrument was set to analyse particles in liquid with magnetic stirrer fitted. A 300 mm focal length lens may be used.

1. Disperse tablet in 100 ml of de-ionised water.

2. Agitate solution for approximately 2 hours.

3. Filter or centrifuge solution to obtain liquor which should be saturated with all ingredients present in the tablet.

4. Disperse second tablet in 50 ml of saturated liquor allowing 3 minutes to fully disperse. Agitate vigorously and remove a sample of the dispersion within 5 minutes adding sufficient quantity to the Malvern PIL cell containing the liquor to obtain an observation value of 0.15–0.30. Analyse sample.

Further examples of tablets according to the invention are described below:

| Example Number | 8 | | 9 | | 10 | |
|---|---|---|---|---|---|---|
| | mg/tablet | %/tablet | mg/tablet | %/tablet | mg/tablet | %/tablet |
| AMTP | 50 | 40 | 50 | 40 | 50 | 40 |
| Lactose | 50 | 40 | 34.5 | 27.6 | 16.2 | 13 |
| Calcium carbonate | | | | | 32.4 | 25.9 |
| Avicel | | | 15 | 12 | | |
| LHPC I1 | 12 | 9.6 | 12 | 9.6 | 12 | 9.6 |
| Veegum | 6.4 | 5.1 | 7 | 5.6 | 7 | 5.6 |
| Explotab | 4 | 3.2 | 4 | 3.2 | 4 | 3.2 |
| Povidone | 1.4 | 1.1 | 1.5 | 1.2 | 2.5 | 2 |
| Magnesium stearate | 1.2 | 1 | 1 | 0.8 | 1 | 0.8 |

| Example Number | 11 | | 12 | | 13 | | 14 | |
|---|---|---|---|---|---|---|---|---|
| | mg/tablet | %/tablet | mg/tablet | %/tablet | mg/tablet | %/tablet | mg/tablet | %/tablet |
| AMTP | 50 | 40 | 100 | 40 | 500 | 40 | 50 | 40 |
| Calcium carbonate | 49.5 | 39.6 | 97 | 38.8 | 51.8 | 41.4 | 48.4 | 38.7 |
| LHPC 11 | 12 | 9.6 | 24 | 9.6 | 12 | 9.6 | 12 | 9.6 |
| Veegum | 7 | 5.6 | 14 | 5.6 | 3.8 | 3 | 7 | 5.6 |
| Explotab | 4 | 3.2 | 8 | 3.2 | 4 | 3.2 | 4 | 3.2 |

| | | | -continued | | | | | |
|---|---|---|---|---|---|---|---|---|
| Povidone | 1.5 | 1.2 | 5 | 2 | 2.5 | 2 | 2.5 | 2 |
| Magnesium stearate | 1 | 0.8 | 2 | 0.8 | 1 | 0.8 | 1 | 0.8 |
| Sodium Lauryl Sulphate | | | | | | | 0.13 | 0.1 |

The tablets defined in Examples 8 to 14 were prepared in accordance with the general method of preparation described above for Examples 1 to 7.

The tablets defined in Examples 8 to 14 were tested in accordance with the procedures described above with the following results:

| EXAMPLE | DIE SIZE (mm) | HARDNESS (kp) | DISPERSION DISINTEGRATION TIME (seconds) |
|---|---|---|---|
| 8 | 7.4 | 2.8 | 65–90 |
| | | 4.4 | 90–107 |
| | | max 6 | 90–105 |
| 9 | 7.4 | 5 | 50–68 |
| | | 8 | 247–257 |
| | | max 13 | — |
| 10 | 7.4 | 3.2 | 81–96 |
| | | 7 | 248–265 |
| | | max 10 | — |
| 11 | 8.6 | 5.8 | 18–23 |
| | | 9.1 | 34–39 |
| | | max 10 | — |
| 12 | 7.4 | 6.4 | 28–32 |
| | | 9.8 | 45–55 |
| | | max 15.4 | 110–130 |
| 13 | 7.4 | 3.4 | 19–23 |
| | | 7.1 | 105–118 |
| | | max 11.3 | 265–270 |
| 14 | 7.4 | 3.2 | 33–35 |
| | | 6.8 | 45–49 |
| | | 9.1 | 60–66 |

We claim:

1. A water-dispersible tablet comprising within the granules of the tablet 4-amino-2-(4-methylpiperazin-1-yl)-5-(2,3,5-trichlorophenyl)pyrimidine together with a pharmaceutically acceptable swellable clay disintegrating agent and a further pharmaceutically acceptable disintegrating agent; and outside the granules, lubricant; to provide a tablet which is capable of dispersing in water within a period of 3 minutes to provide a dispersion which is capable of passing through a sieve screen with a mesh aperture of 710 μm in accordance with the test for dispersible tables defined in the British Pharmacopoeia, 1988, Volume II, page 895.

2. A tablet as claimed in claim 1 containing 15 to 50% w/w of 4-amino-2-(4-methylpiperazin-1-yl)-5-(2,3,5-trichlorophenyl)pyrimidine.

3. A tablet as claimed in claim 1 or claim 2 in which the swellable clay is a magnesium aluminium silicate.

4. A tablet as claimed in any of the preceding claims containing 3 to 10% w/w of the swellable clay.

5. A tablet as claimed in any of the preceding claims in which the further disintegrating agent is selected from sodium starch glycollate, low hydroxypropyl cellulose (LHPC) and low hydroxypropylmethylcellulose (LHPMC).

6. A tablet as claimed in any of the preceding claims containing 1 to 5% w/w of the further disintegrating agent.

7. A tablet as claimed in any of the preceding claims containing a filler.

8. A tablet as claimed in claim 7 in which the filler is calcium carbonate.

9. A tablet as claimed in claim 7 or claim 8 containing 25 to 60% w/w of the filler.

10. A tablet as claimed in any of the preceding claims containing a povidone binder.

11. A process for the preparation of a water-dispersible tablet comprising within the granules of the tablet 4-amino-2-(4-methylpiperazin-1-yl)-5-(2,3,5-trichlorophenyl) pyrimidine ("AMTP"), together with a pharmaceutically acceptable swellable clay disintegrating agent and a further disintegrating agent and outside the granules, lubricant, which process comprises bringing AMTP into association with the swellable clay and further disintegrating agent in the formation of tablet granules and blending the granules with lubricant and optionally other carrier or excipients to provide a water-dispersible tablet which is capable of dispersing in water within a period of 3 minutes to provide a dispersion which is capable of passing through a sieve screen with a mesh aperture of 710 μm in accordance with the test for dispersible tablets defined in the British Pharmacopoeia, 1988, Volume II, page 895.

12. A water-dispersible tablet as claimed in any of claims 1 to 10 for the treatment or preparation of neurodegenerative or other neurological disorders of the central nervous system, the aetiology of which includes excessive release of neurotransmitter glutamate.

13. A water-dispersible tablet comprising within the granules of the tablet AMTP together with a pharmaceutically acceptable swellable clay disintegrating agent and outside the granules, lubricant; to provide a tablet which is capable of dispensing in water within a period of 3 minutes to provide a dispersion which is capable of passing through a sieve screen with a mesh aperture of 710 μm in accordance with the test for dispersible tablets defined in the British Pharmacopoeia, 1988, Volume II, page 895.

* * * * *